United States Patent [19]

Kallies

[11] 4,248,973
[45] Feb. 3, 1981

[54] CAPILLARY TUBE INDICATOR FOR THE DETERMINATION OF UREA CONCENTRATIONS

[75] Inventor: Karl-Heinz Kallies, Sebnitz, German Democratic Rep.

[73] Assignee: Veb Arzneimittelwerk Dresden, Radebeul, German Democratic Rep.

[21] Appl. No.: 973,075

[22] Filed: Dec. 22, 1978

[30] Foreign Application Priority Data

Apr. 11, 1977 [DD] German Democratic Rep. ... 201873

[51] Int. Cl.$^3$ .................. C12Q 1/58; G01N 33/52; G01N 33/62
[52] U.S. Cl. ...................... 435/296; 23/924; 422/56; 422/58; 435/12; 435/805
[58] Field of Search ............... 422/56, 58; 435/12, 435/805; 23/924

[56] References Cited

U.S. PATENT DOCUMENTS 3,249,513 5/1966 Babson .................. 435/12
3,768,978 10/1973 Grubb .................... 422/56

Primary Examiner—Sidney Marantz
Attorney, Agent, or Firm—Michael J. Striker

[57] ABSTRACT

A capillary tube indicator for determination of urea concentrations, which permits a simple measurement of the sample without auxiliary aids, provides an easily readable measurement, and does not require the addition of buffers, alkali carbonates or hydroxides. The indicator includes a capillary tube of glass or plastic into which a specially prepared indicator strip is inserted. The reaction system of the indicator strip includes a partially purified urease preparation and 1 to 15% of a saccharide or polysaccharide, preferably glucose. The indicator strip also has zones treated with alkali-sensitive dye, applied so as to give either quantitative or semiquantitative readings of urea concentration.

12 Claims, 3 Drawing Figures

CAPILLARY TUBE INDICATOR FOR THE DETERMINATION OF UREA CONCENTRATIONS

BACKGROUND OF THE INVENTION

The present invention relates to the field of medicine, and in particular to the determination of urea levels in blood and serum. More specifically, the invention concerns a novel type of indicator for the simple and rapid determination of urea concentrations.

For determining the concentration of urea in blood and serum samples, use has been made of the enzymatic reaction with urease, the products of which are carbon dioxide and ammonia. In some prior art embodiments, determination of the change in pH is effected in the urease reaction zone of the indicator strip using pH indicator dyes (DE-AS No. 1,498,601 and DE-AS No. 1,598,756). In other systems, measurement takes place in a separate indicator zone of the liberation of ammonia gas) DE-AS No. 1,245,619 and DE-AS No. 2,249,647). Calibration of the indicator compounds may be effected through the use of organic acids. From this data, the urea concentration of the sample may be determined according to the parameters of the urease reaction.

In order to improve the stability of the reaction and of the dyes, known additives have been employed in some prior art embodiments. For example, an alkali buffering system with the addition of organic acid and stabilizing agents is known to be an effective means of increasing the accuracy of determinations.

Increasingly, tests of urea levels are being performed on whole blood or serum in ambulances and at sickbeds. For a quantitative or semiquantitative measurement, an accurate pipetting of between 0.01 and 0.1 ml or sample is required. The indicator strips must be kept in a refrigerator if they are to be used over a long period of time, as they are sensitive to basic contaminants in the air. The indicator zone containing dyes is calibrated using printed or stencilled gauges, but the meniscus effect and the indefiniteness of the measurement line hampers accurate determinations by an inexperienced person.

Added to these drawbacks is the fact that the preparation of indicator strips with numerous reagents is complicated and requires high standards of quality control to insure reproducibility. As the urease activity is markedly reduced by the presence of traces of certain known metals, the purity of the compounds used must also be maintained to a great degree.

SUMMARY OF THE INVENTION

It is a goal of the invention to prepare a capillary tube indicator which allows for the measurement of a required amount of blood or serum and for determination of the urea concentration in the sample without requiring auxiliary means.

For the inventive measuring system, a capillary tube of glass or plastic can be used, which at the lower end thereof is marked with a line, preferably colored, indicating the amount of sample to be used. The position of the line is determined by the inner diameter of the capillary, the type of carrier material used for the indicator strip and the length of the reaction zone on the indicator strip. Found to be suitable are capillaries with lengths between 40 and 120 mm, preferably about 60 mm, and inner diameters of 1-3 mm, preferably 2.5 mm. Alternatively, a region above the mark can have an interior diameter of up to 10 mm, creating an enlarged reaction chamber.

The indicator strip located within the capillary carries a reaction zone and one or more indicator zones of the same or of different indicator dye solutions. The indicator zones are of widths between 1 and 5 mm, preferably 2 mm, and are located on the indicator strip so as to allow for untreated bands of 1 to 10 mm between respective indicator bands.

The indicator strips may be made of various natural or synthetic fibrous materials, as long as they are suitably adsorbent and do not effect the reaction system. Preferably, filter paper of 60 to 400 $g/m^2$ weight is employed. The dimensions of the reaction zone and the indicator zone(s) are determined by the thickness of the filter paper and the applied active enzyme.

The use of a capillary facilitates the measurement of an accurate sample of between 10 and 30 microliters even by inexperienced or lay assistants, which can be performed anywhere without the need for auxiliary means. External contaminants can affect the protected indicator strip in the capillary only under the most extreme conditions. The protected environment of the capillary tube also insures controlled gas release and diffusion.

As the release of ammonia is not linear with the urea concentration, the indicator zones can either be arranged so as to take this fact into account, or to read the amount of gas released directly and evaluate the concentration by a standard calibration table. An indicator strip calibrated to read the lowermost physiological limit of urea concentration further provides an internal check on the quality of the particular capillary tube indicator. The employment of multiple indicator zones further simplifies the evaluation of results by inexperienced persons. Use of various indicator dyes improves color contrast, simplifies evaluation further and makes the measurements more precise.

The indicator strips of the inventive capillary tube indicator are further distinguished by the addition of 1 to 15% of a saccharide or polysaccharide to the urease preparation in the reaction zone. The use of glucose as the saccharide has been found to be particularly advantageous.

Urease preparations that are not highly purified tend to become water-repellent when applied to absorbent carriers; thus, the reaction zone does not absorb the serum or blood quickly enough for accurate determinations. The addition of saccharides or polysaccharides eliminates this problem and further tends to stabilize the enzyme activity of the reaction zone under normal conditions.

Although not necessary, cooling of the capillary tube indicators in a refrigerator during the determination may be advantageous.

The indicator strips are further distinguishable from the prior art in that they employ only a slightly purified urease preparation, and do not require the addition of buffers, alkali carbonates and/or hydroxides. With the novel indicator strips, the reaction time is shortened without any decrease in the accuracy of the measurement.

As indicator dyes, substances suitable for use as alkali indicators are mandated. The dye "brilliant-yellow", which turns red in the presence of ammonia, has been found to be particularly advantageous.

In order to prevent absorption of the blood or serum into the indicator zones, solutions of hydrophobic materials useful in the paper and textile industries can be employed. These solutions are applied in a band of between 2 and 5 mm on the indicator strips below the first indication zone. One suitable preparation is a 20% solution of stearic acid in carbon tetrachloride.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

EXAMPLE 1

Figure 1:
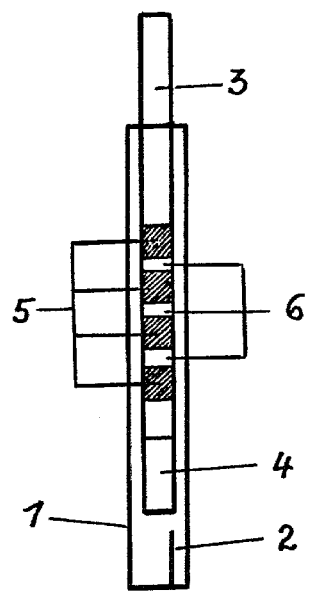
FIG. 1 illustrates a capillary tube indicator in which the inner diameter remains constant.

This example will be described with reference to the embodiment of FIG. 1.

A capillary tube 1 of plastic with an interior diameter of 2.5 mm and a length of 60 mm is used. A mark 2 is located 4 mm from the bottom. For preparing the indicator strip 3 a piece of filter card board with a surface weight of 200 g/m² is chosen. The reaction zone is impregnated with the following mixture:

| Urease preparation | 4,500 µ/mg = 1000 µ |
|---|---|
| Glucose | 1 g |
| Distilled water | 10 ml. |

A 20 mm strip of the filter cardboard is impregnated with this solution. Simultaneously, a solution of 20% stearic acid in carbon tetrachloride is applied in a 4 mm strip above the reaction zone. This helps prevent absorption of the serum or blood into the indicator zones. Alternatively, other known hydrophobic substances can be utilized in strips of between 2 and 5 mm.

Simultaneously with the application of the urease solution and the hydrophobic mixture, indicator signal bands 5 are applied above the hydrophobic zone, according to examples 2–4. Their arrangement is determined by the type of measurement (quantitative or semiquantitative) desired.

The filter cardboard so prepared is then cut up into narrow indiator strips for placement within a capillary 1.

The indicator strip 3 is pulled about 10 mm above the mark 2 when a urea test is to be made. The marked end of the capillary 1 is dipped into the sample. If the capillary is filled over the mark 2, the excess can be absorbed by a small piece of filter paper, leading to simple correction. The filter paper is then dropped back to the level of mark 2 and the determination made at 25° C. after 15 minutes.

EXAMPLE 2

A solution of 10 mg of the dye brilliant yellow in 10 ml of ethanol is applied in 2 to 3 mm bands above the hydrophobic band of the above filter cardboard, leaving 1 to 2 mm strips untreated between the indicator bands. Using such a strip with 5 such indicator bands, a measurement is effected as in Example 1. A first assessment of enhanced urea level can be made after about 5 minutes. Each indicator band represents a known urea concentration, which is determined by its width and the width of the spaces between bands. These values can be printed on the indicator strip or the capillary, or alternatively a calibration table may be provided.

EXAMPLE 3

The following solutions are used as indicators:

| Solution A | bromocresol green | 40 mg |
|---|---|---|
| | tataric acid | 100 mg |
| | ethanol | 10 ml |
| Solution B | brilliant yellow | 40 mg |
| | ethanol | 10 ml |

The above solutions are applied to the indicator strips in the following order:

1. Solution A, in a 2 to 3 mm strip; untreated strip, 1 mm;
2. Solution B, in a 2 to 3 mm strip; untreated strip, 1 mm;
3. Solution A, in a 2 to 3 mm strip; untreated strip, 2 mm;
4. Solution A, in a 2 to 3 mm strip; untreated strip, 3 mm;
5. Solution B, in a 2 to 3 mm strip.

The untreated strips could also be as large or larger than the indicator zones. For any strip prepared in this manner, the corresponding urea concentration values can either be given in a calibration table or printed on the capillary or indicator strip.

The use of an indicator dye which turns red allows for a more dramatic indication of enhanced urea levels.

The reaction occurs at 25° C. and requires about 15 minutes before final evaluation of the urea concentration.

EXAMPLE 4

A solution of 30 mg bromocresol green, 60 mg tataric acid and 10 ml ethanol is applied in bands of 1 to 3 mm width above the hydrophobic zone of the filter strip. The number of zones 5 and the width of the untreated zones 6 determines the accuracy of the measurement and the range of concentrations evaluated.

If between the first and second indicator zones an untreated strip of 1 mm is used, between the second and third an untreated strip of 2 mm, and between the third and fourth an untreated strip of 4 mm, the following values are indicated: first signal zone, up to 20 mg urea nitrogen; second signal zone, 30 mg urea/nitrogen; third signal zone, 45 mg urea/nitrogen; and fourth signal zone, 60 mg urea/nitrogen.

Figure 2:
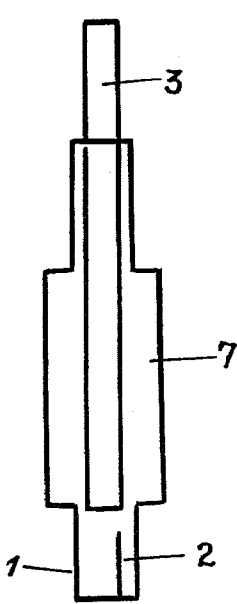
FIGS. 2 and 3 show capillaries with portions of increased inner diameter, forming enlarged reaction chambers.
Figure 3:
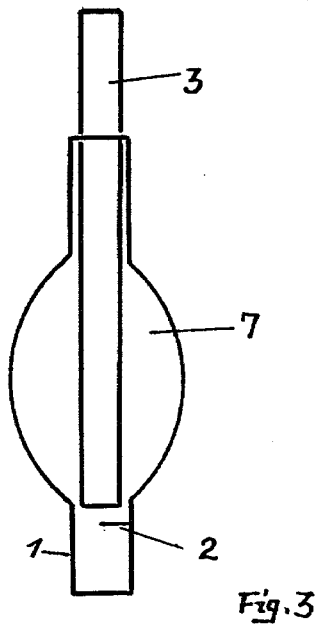

Alternatively, a capillary tube 1 with an enlarged reaction chamber as illustrated in FIGS. 2 and 3 can be employed. The embodiment in FIG. 2 has a 10 mm long section with an inner diameter of 2.5 mm in the area of the mark 2, a 30 mm long section which is enlarged and forms a chamber 7 having a constant inner diameter of 7 mm, and a final segment of 20 mm length wherein the inner diameter is again reduced to 2.5 mm.

By using a capillary of this type, the reaction time may be reduced to about 7 minutes.

The embodiment of FIG. 3 corresponds essentially to that of FIG. 2 and has capillary-tube sections corresponding in length and diameter essentially to those in FIG. 2. The exception is the enlarged chamber 7a which here is not of constant inner diameter but, instead, is of barrel-shaped configuration and increases in inner diameter from its opposite ends (where the diameter is 2.5 mm) to midway between these ends where the inner diameter is largest (i.e. up to 10 mm).

Again, using the embodiment of FIG. 3, the reaction time may be reduced to about 7 minutes.

It will be understood that each of the elements described above, or two or more together, may also find a useful application in other types of constructions differing from the types described above.

While the invention has been illustrated and described as embodied in a capillary tube indicator for the determination of urea concentrations, it is not intended to be limited to the details shown, since various modifications and structural changes may be made without departing in any way from the spirit of the present invention.

Without further analysis, the foregoing will so fully reveal the gist of the present invention that others can by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A capillary tube indicator for the micro determination of urea concentrations comprising a capillary tube having a marking line near one end to indicate sample level; an indicator strip inserted within said capillary tube; a reaction system applied in a zone at one end of said indicator strip comprising a partially purified urease preparation and between substantially 1 and 15% of a saccharide or polysaccharide; and above said reaction system zone at least one indicator dye sensitive to alkali applied to said indicator strip in a plurality of zones for providing a visual indication of the urea concentration with untreated bands of the indicator strip separating said indicator zones and said reaction system zone from said first indicator zone.

2. An indicator as defined in claim 1, wherein said capillary tube is glass or plastic.

3. An indicator as defined in claim 1, wherein said capillary tube has a length of between substantially 40 and 120 mm and an inner diameter of between substantially 1 and 3 mm.

4. An indicator as defined in claim 1, wherein said capillary tube has a length of 6 mm and an inner diameter of 2.5 mm.

5. An indicator as defined in claim 1, wherein said capillary tube has a portion having an expanded inner diameter of up to 10 mm.

6. An indicator as defined in claim 1, wherein said indicator strip is of natural or synthetic fiber.

7. An indicator as defined in claim 1, wherein said indicator strip is of filter paper having a weight of substantially 60 to 400 g/m$^2$.

8. An indicator as defined in claim 1, wherein said saccharide or polysaccharide is glucose.

9. An indicator as defined in claim 1, wherein said indicator dye is brilliant-yellow.

10. An indicator tube as defined in claim 1, wherein said indicator dye is bromocresol green.

11. An indicator tube as defined in claim 1, wherein said indicator dye zones have a width of between substantially 1 to 5 mm, and said untreated zones have a width of between substantially 1 to 10 mm.

12. An indicator as defined in claim 11, wherein said indicator dye zones have a width of 2 mm.

* * * * *